(12) United States Patent
Labance

(10) Patent No.: US 10,449,181 B2
(45) Date of Patent: Oct. 22, 2019

(54) TREATMENT OF AUTISM AND AUTISM SPECTRUM DISORDERS (ASD)

(71) Applicant: Sarah E. Labance, Vernon, NJ (US)

(72) Inventor: Sarah E. Labance, Vernon, NJ (US)

( * ) Notice: Subject to any disclaimer, the term of this patent is extended or adjusted under 35 U.S.C. 154(b) by 0 days.

(21) Appl. No.: 15/687,111

(22) Filed: Aug. 25, 2017

(65) Prior Publication Data

US 2018/0055827 A1     Mar. 1, 2018

Related U.S. Application Data

(60) Provisional application No. 62/379,331, filed on Aug. 25, 2016.

(51) Int. Cl.
    *A61K 31/437*     (2006.01)

(52) U.S. Cl.
    CPC .................. *A61K 31/437* (2013.01)

(58) Field of Classification Search
None
See application file for complete search history.

(56) References Cited

U.S. PATENT DOCUMENTS

| | | | |
|---|---|---|---|
| 2007/0112017 A1 | 5/2007 | Barlow et al. | |
| 2007/0238765 A1 | 10/2007 | Lin et al. | |
| 2010/0136004 A1 | 6/2010 | Mei et al. | |
| 2010/0144863 A1 * | 6/2010 | Hublot | C07D 317/54 514/464 |
| 2015/0313913 A1 | 11/2015 | Catterall et al. | |

FOREIGN PATENT DOCUMENTS

| | | | | |
|---|---|---|---|---|
| WO | WO-2008148023 A2 * | 12/2008 | | A61K 38/45 |
| WO | 2015095783 | 6/2015 | | |

OTHER PUBLICATIONS

Poil, S. et al., Eur. J. Neurosci. 2011, vol. 34, pp. 394-403.*
Fisher, J. Neuropharmacol. 2009 vol. 56 pp. 190-197.*
Self, T. et al, Language, Speech, and Hearing Services in Schools vol. 41, pp. 367-75 2010.*
Han, S. Neuron 2014 vol. 81, pp. 1282-1289.*
Han, Autistic-like behaviour in Scn1a +/− mice and rescue by enhanced GABA-mediated neurotransmission, Nature, Sep. 20, 2012, pp. 385-390, vol. 489, Mcmillan Publishers.

* cited by examiner

*Primary Examiner* — Heidi Reese
(74) *Attorney, Agent, or Firm* — Gearhart Law, LLC.

(57) ABSTRACT

It is provided herein a method of treating an Autism Spectrum Disorder (ASD) in a patient by administering to the patient a therapeutically effective amount of a composition of a compound that is a positive allosteric modulator of the $GABA_A$ receptor having a selectivity towards an α1 subunit of the receptor.

2 Claims, No Drawings

TREATMENT OF AUTISM AND AUTISM SPECTRUM DISORDERS (ASD)

CLAIM OF PRIORITY

This application claims priority to U.S. application Ser. No. 62/379,331 filed on Aug. 25, 2016, the contents of which are hereby fully incorporated by references in its entirety.

FIELD OF THE EMBODIMENTS

This invention relates to methods for treating Autism or Autism Spectrum Disorder in a subject in need of treatment or at risk of said disorders.

BACKGROUND OF THE EMBODIMENTS

Recent research suggests (Baron-Cohen et al., 2009; Schechter and Grether, 2008; Thomas et al., 2011; Zaroff and Uhm, 2011) that approximately 0.6-1.5% of the general population may be diagnosed as having Autism or Autism Spectrum Disorder (thereafter "ASD"), which are neurodevelopmental disorders that are distinguished and characterized by deficits in social reciprocity, communication impairments, and restricted, repetitive interests and behaviors (World Health Organization, 1993). Other symptoms, such as atypical eating, are common in autistic children. In addition, symptoms for ASD, as defined in the DSM-V, are likely present in early childhood and collectively limit and hinder everyday functioning.

For instance, patients of severe Asperger's Syndrome, one of the Autism Spectrum Disorders can have one or more of the following primary symptoms:

Extreme difficulty with social interaction
Inability to have metered speech
Difficulty making conversation
Inability to make eye contact
Profound need to conform to a rigid schedule and great difficulty deviating from it
Difficulty with information processing
Sensitivity to novel stimuli
Difficulty bonding
Anxiety
Hypersensitivity to touch
Difficulty transitioning
Difficulty multitasking
Severe ruminations
Severe obsessional thoughts and actions
Fixations
Severe perseveration
Seizures
Hypergraphia
Jamai vu' and deja vu'

In particular, ASD patients report experiencing continuous pain, which has been described by some as "psychic/phantom" pain (i.e., severe and extremely debilitating pain that is neither physical nor emotional). Some studies of ASD patients have pointed to the potential underlying cause as ASD patients having, inter alia, an amplified pain sensitivity and/or observer perception of pain. More discussions of ASD-related pain can be found in the literature: see e.g., Allely (2013), Moore (2015) and Clarke (2015).

Past and the Present Methods of Autism Treatments

Therapies for treatment of autism include conventional, intensive Applied Behavioral Analysis (ABA) therapy as well as a host of alternative approaches, including a gluten-free and casein-free (GFCF) diet, hyperbaric oxygen chambers, chelation, aroma therapies, electro-magnetics, spoons rubbed on his body, multivitamin therapy, B-12 shots and a range of prescription psychosomatic drugs.

In spite of the prior research and the knowledge, nonetheless, there is no cure for autism, but a number of therapeutic agents developed for other conditions have been found to be, to some extent, helpful in treating a limited number of the symptoms and behavioral problems. Examples of such therapeutic agents used to treat symptoms associated with autism (such as hyperactivity, impulsivity, attention difficulties, and anxiety) include: serotonin re-uptake inhibitors (e.g. clomipramine (Anafranil), fluvoxamine (Luvox) and fluoxetine (Prozac)). Studies show that they reduce the frequency and intensity of repetitive behaviors, decrease irritability, tantrums and aggressive behavior, improvements in eye contact and responsiveness. Other drugs, such as Elavil, Wellbutrin, Valium, Ativan and Xanax, are also being tried to decrease the behavioral symptoms.

The extensively studied psychopharmacologic agents in ASD have been anti-psychotic medications developed for treating schizophrenia. These therapeutic agents do decrease hyperactivity, stereotypic behaviors, withdrawal and aggression in autistic children. Four anti-psychotic medications that have been approved by the FDA are clozapine (Clozaril), risperidone (Risperdal), olanzapine (Zyprexa) and quetiapine (Seroquel). However, only risperidone has been investigated in a controlled study of adults with autism. Stimulants, such as Ritalin, Adderall, and Dexedine, used to treat hyperactivity in children with ADHD have also been prescribed for children with autism. They are said to increase focus, and decrease impulsivity and hyperactivity in autism; regrettably, adverse behavioral side effects are often observed.

US Patent Application No. 2009/0048348 A1 by M. Chez disclosed that administering effective doses of a NMDA-receptor antagonist or a pharmaceutically acceptable salt thereof improves frontal executive functions associated with autistic symptoms, including, but not limited to, speech expression and decreased perseveration without any side effects associated.

Currently, autism spectrum disorders are treated by using: inter alia, applied behavior analysis or other behavior modification techniques; dietary alteration (e.g., a gluten or casein free diet); large doses of vitamin B6 in combined with magnesium; medications specific symptoms (e.g., anxiety and depression) and include agents (e.g., fiuoxetine, fiuvoxamine, sertraline and clomipramine); and, antipsychotic medications (e.g., chlorpromazine, thioridazine, and haloperidol) have been used to treat behavioral problems. Anti-convulsants (e.g., arbamazepine, lamotrigine, topiramate, and valproic acid) have been given to prevent seizures.

Numerous studies have reported differences in brain anatomy and function in individuals with ASD (See e.g., Craig et al., 2007; Ecker et al., 2010; Hallahan et al., 2009), but the underlying molecular basis of the disease condition remains unclear. ASD is now viewed as a heterogeneous set of disorders, which can be caused by various genetic, epigenetic and environmental factors, but emerging evidence suggests that an imbalance between excitatory glutamate and inhibitory gamma-amino-butyric-acid (GABA) neurotransmission may form a final common pathway in ASD.

In particular, defects in GABA transmission, leading to brain hyperexcitability, have been hypothesized to underlie the symptoms of ASD (Pizzarelli and Cherubini, 2011; Rubenstein and Merzenich, 2003; Yizhar et al., 2011).

GABA$_A$ receptors (GABA$_A$ R) are pentameric assemblies from a pool of different subunits ($\alpha$1-$\alpha$6, $\beta$1-3, $\gamma$1-3, $\delta$, $\epsilon$, $\pi$, $\theta$) that form a Cl-permeable channel that is gated by the neurotransmitter $\gamma$-aminobutyric acid (GABA). Various pharmacological effects, including anxiety disorders, epilepsy, insomnia, pre-anesthetic sedation, and muscle relaxation, are mediated by different GABA$_A$ subtypes. More specifically, GABA receptor genes have been associated with autism in linkage and copy number variation studies. Fewer GABA receptor subunits have been observed in the post-mortem tissue of autistic individuals. Further, it's been shown that neurotransmitter GABA signaling is disrupted across heterogeneous mouse models of autism.

US Patent Application No. 2015/0313913 A1 by W. A. Catterall, entitled "Positive allosteric modulators of the GABA$_A$ receptor in the treatment of autism," provided various methods and formulations for treating an Autism Spectrum Disorder using low doses of an agent that enhances signaling through the GABA receptor. These included $\alpha$2 and/or $\alpha$3 selective GABA$_A$ receptor positive allosteric modulators, but specifically avoided targeting $\alpha$1 GABA$_A$ receptors.

US Patent Application No. 2010/0136004 A1 by L. Mei et al, provided methods and compositions for modulating GABA release in a subject are provided. A preferred embodiment provides a composition containing an effective amount of an ErbB4 ligand, which can be an agonist ligand or an antagonist ligand depending on the disorder to be treated, to reduce or inhibit GABA release in the subject. Representative disorders that can be treated include, inter alia, autism. By so increasing GABA release, a sedative effective can be induced in the subject.

PCT Patent Application No. WO 2015/095783 A1 by B. Mekonnen et al., disclosed benzodiazepine derivatives, compositions comprising therapeutically effective amounts of those benzodiazepine derivatives and methods of using those derivatives or compositions in treating cognitive impairment associated with central nervous system (CNS) disorders. In particular, it relates to the use of a $\alpha$5-containing GABA$_A$ receptor agonist (e.g., a $\alpha$5-containing GABA$_A$ receptor positive allosteric modulator) in treating cognitive impairment associated with central nervous system (CNS) disorders in a subject in need or at risk thereof, including, inter alia, autism spectrum disorders.

None of the art described above addresses all of the issues that the present invention does, because, regrettably, the aforementioned treatments for autism spectrum and related disorders are mainly symptomatic. They have proven futile in allowing patients to become symptom free, or disorder free. As a result, there is an unmet need in the art for alternative and more effective treatments for autism spectrum disorders and related illnesses.

The present invention relates to methods and regimens of treating autism and autism related spectrum disorders, and more particularly, relates to methods and regimens of administering, through oral dosing, effective amounts of a sub-type selective, positive allosteric modulator (thereafter "PAM") of the GABA$_A$ receptor, zolpidem, or pharmaceutically acceptable salts thereof, and, optionally, in conjunction with other known adjuvant anti-autism therapeutic agents, to treat ASD in humans.

SUMMARY OF THE EMBODIMENTS

In one of the embodiments, the present invention provides a method of treating an Autism Spectrum Disorder or an indicium thereof, in a subject in need thereof, which method comprises administering to said subject a therapeutically effective amount of a composition comprising a compound and a pharmaceutically acceptable carrier, wherein said compound is a positive allosteric modulator of the GABA$_A$ receptor, or a pharmaceutically acceptable salt thereof.

In another one of the embodiments, the present invention provides that the positive allosteric modulator (i.e., PAM) of the GABA$_A$ receptor in the aforementioned method can be a full, or a partial, agonist at the GABA$_A$ receptor.

In one of the aspects of the present invention, the aforementioned PAM of the GABA$_A$ receptor can a short-acting, or a long-acting, agonist at the GABA$_A$ receptor.

In another of the aspects of the present invention, the aforementioned PAM of the GABA$_A$ receptor of this embodiment has a preferential efficacy (or functional selectivity) at the GABA$_A$ receptors comprising an $\alpha$1 subunit.

In yet another of the aspects of the present invention, the aforementioned PAM of the GABA$_A$ receptor has a preferential efficacy/functional selectivity at the GABA$_A$ receptors comprising an $\alpha$1 subunit.

In yet another of the aspects of the present invention, the aforementioned PAM of the GABA$_A$ receptor has a preferential efficacy/functional selectivity at the GABA$_A$ receptors comprising an $\alpha$1 subunit and an $\alpha$2, $\alpha$3 or $\alpha$5 subunit, or a combination thereof.

In still another one of the embodiments, the present invention provides that the PAM of the GABA$_A$ receptor in the aforementioned method is a compound belonging to the benzodiazepine class of compounds selected from the group consisting of diazepam, alprazolam, lorazepam, estazolam, temazepam, chlordiazepoxide, clonazepam, diazepam, flurazepam, quazepam, clorazepate, oxazepam, midazolam, triazolam or pharmaceutically acceptable salts thereof.

In yet another one of the embodiments, the present invention provides that the PAM of the GABA$_A$ receptor in the aforementioned method is a compound belonging to the non-benzodiazepine class of compounds selected from the group consisting of zolpidem, zaleplon, zopiclone, eszopiclone, (S)-desmethylzopiclone, bretazenil, imidazenil, FG 8205, abecarnil, NS 2710, pagoclone, stiripentol, RWJ-51204, ROD-188, CGS-8216, CGS-9896, CGS-13767, CGS-20625 and GBLD-345 or pharmaceutically acceptable salts thereof.

In a preferred embodiment, the present invention provides that the PAM of the GABA$_A$ receptor in the aforementioned method is zolpidem, or pharmaceutically acceptable salts thereof. Furthermore, the therapeutically effective daily amount of zolpidem in the aforementioned method comprises zolpidem (in the form of AMBIEN®) within a dose range of 0.01 mg to 120 mg, and more specifically, of at least about 30 mg every about 3.5 hours (around the clock).

One of the aspects of the present invention concerns a method for treating an ASD, which disease state comprises at least having one symptom selected from the group consisting of: persistent deficits in social communication and poor social interactions across multiple contexts; repetitive patterns of behavior(s), interests, or activities; cognitive deficit and impaired language development.

Another of the aspects of the present invention concerns a method for reducing or ameliorating at least one indicium of an ASD, which method comprises administering effective amounts of a compound that increases the response of the GABA$_A$ receptor to endogenous GABAergic transmission, whereby at least one indicium is reduced or ameliorated, which indicium of the ASD is selected from the group consisting of: persistent deficits in social communication and poor social interactions across multiple contexts; repetitive patterns of behavior(s), interests, or activities; cognitive deficit and impaired language development, and more preferably, the at least one indicium of the ASD is repetitive patterns of behavior(s) or activities, impaired language development and/or impaired social interactions.

In yet another one of the embodiments, the present invention provides that the compound that increases the response of the $GABA_A$ receptor to endogenous GABAergic transmission for reducing or ameliorating at least one indicium of the ASD in the aforementioned method is a subunit-selective PAM of the $GABA_A$ receptor of the structural class of a benzodiazepine. The subunit-selectivity mentioned here can be related to functional selectivity, or affinity/binding selectivity, or both.

In yet another one of the embodiments, the present invention provides that the compound that increases the response of the $GABA_A$ receptor to endogenous GABAergic transmission for reducing or ameliorating at least one indicium of an ASD in the aforementioned method is a subunit-selective PAM of the $GABA_A$ receptor of the structural class of a non-benzodiazepine. The subunit-selectivity mentioned here can be related to functional selectivity, or affinity/binding selectivity, or both.

In yet another one of the embodiments, the present invention provides a pharmaceutical composition comprising a formulation in a pharmaceutically acceptable carrier of a compound that is a subunit-selective positive allosteric modulator of the $GABA_A$ receptor. The subunit-selectivity mentioned here can be related to functional selectivity, or affinity/binding selectivity, or both.

In yet another aspect of the present invention, the structural class of the aforementioned compound is a benzodiazepine.

In yet another aspect of the present invention, the structural class of the aforementioned compound is a non-benzodiazepine.

In yet another aspect of the present invention, the aforementioned formulation is in the form of a tablet, a capsule, a suspension, or a solution.

In yet another aspect of the present invention, the aforementioned formulation comprises a compound that is a full agonist at the $GABA_A$ receptor.

In yet another aspect of the present invention, the aforementioned formulation comprises a compound that is a partial agonist at the $GABA_A$ receptor.

In yet another aspect of the present invention, the aforementioned formulation of a benzodiazepine compound or a non-benzodiazepine compound has a preferential efficacy or functional selectivity at a $GABA_A$ receptor comprising an $\alpha 1$ subunit.

In yet another aspect of the present invention, the aforementioned formulation of a benzodiazepine compound or a non-benzodiazepine compound has a preferential efficacy or functional selectivity at a $GABA_A$ receptor comprising an $\alpha 1$ subunit and an $\alpha 2$, $\alpha 3$ or $\alpha 3$ subunit or a combination thereof.

In yet another aspect of the present invention, the aforementioned formulation comprises a compound that is a short-acting PAM of the $GABA_A$ receptor.

In yet another aspect of the present invention, the aforementioned formulation comprises a compound that is a long-acting PAM of the $GABA_A$ receptor.

In yet another one of the embodiments, the present invention provides that the aforementioned formulation of a benzodiazepine compound is selected from the group consisting of diazepam, alprazolam, lorazepam, estazolam, temazepam, chlordiazepoxide, clonazepam, diazepam, flurazepam, quazepam, clorazepate, oxazepam, midazolam, triazolam or pharmaceutically acceptable salts thereof.

In a preferred embodiment, the present invention provides that the aforementioned formulation of a benzodiazepine compound is diazepam and the composition comprises a dose of diazepam within the range of 0.01 mg to 40 mg.

In yet another one of the embodiments, the present invention provides that the aforementioned formulation of a non-benzodiazepine compound is selected from the group consisting of zolpidem, zaleplon, zopiclone, eszopiclone, (S)-desmethylzopiclone, bretazenil, imidazenil, FG 8205, abecarnil, NS 2710, pagoclone, stiripentol, RWJ-51204, ROD-188, CGS-8216, CGS-9896, CGS-13767, CGS-20625 and GBLD-345 or pharmaceutically acceptable salts thereof.

In a preferred embodiment, the present invention provides that the aforementioned formulation of a non-benzodiazepine compound is zolpidem and said composition comprises a daily dose of zolpidem within the range of 0.01 mg to 120 mg.

In a more preferred embodiment, the present invention provides that the aforementioned formulation of a non-benzodiazepine compound is zolpidem and the therapeutically effective daily dose of zolpidem is at least 30 mg every 3.5 hour (around the clock).

It is an object of the present invention to provide a method based on a rationale design of treating an Autism Spectrum Disorder, or an indicium thereof, in a patient by administering to the patient a therapeutically effective amounts of a composition comprising a compound and a pharmaceutically acceptable carrier, wherein the compound is a subunit-selective positive allosteric modulator of the $GABA_A$ receptors.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Definitions

As used above, and throughout this disclosure, the following terms, unless otherwise indicated, shall be understood to have the following meanings, which are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from a dictionary known to those of skill in the art, such as the Oxford Dictionary of Biochemistry and Molecular Biology (Ed. Anthony Smith, Oxford University Press, Oxford, 2004). If a definition is missing, convention definition as known to one skilled in the art controls.

"Patient" includes both human and animals.

"Mammal" means humans and other mammalian animals.

For the purpose of this invention, the term "agent that increases the endogenous GABAergic transmission" refers to an agent that increases opening of the GABA receptor chloride channel thereby inducing hyperpolarization of the post-synaptic neuron. In some embodiments, the agent that increases the endogenous GABAergic transmission is a $GABA_A$ receptor agonist. In other embodiments, the agent that increases the endogenous GABAergic transmission is a positive allosteric modulator of the $GABA_A$ receptor. Here, the term "agonist" should be understood as encompassing both full and partial agonists, but does not encompass inverse agonists (such as those acting at the benzodiazepine, BZ, site), whereby the term "partial agonist" should be understood as a an agent that produces a lower maximal response at full receptor occupancy than an agent considered to be a "full agonist." A partial agonist is not defined by a lower affinity for a binding site, but rather a "partial agonist" is defined by its ability to competitively inhibit the responses produced by a full agonist at higher concentrations (e.g., to reduce the maximal response to that of the partial agonist).

For the purpose of this invention, the term "positive allosteric modulator" is defined as an agent that binds a receptor (e.g., the $GABA_A$ receptor), at a site other than that bound by the endogenous neurotransmitter (e.g., gamma-aminobutyric acid, GABA) and enhances the activity of the receptor in response to the endogenous neurotransmitter, for example, by increasing the frequency of opening of the GABA chloride channel. GABA is an inhibitory neurotransmitter that, when bound to the $GABA_A$ receptor facilitates entry of chloride ions into the neuron. The increase in chloride ions hyperpolarizes the membrane of the neuron. This completely or substantially reduces the ability of the neuron to generate an action potential. A positive allosteric modulator need not activate the chloride channel of the GABA receptor directly (e.g., does not substitute for the neurotransmitter GABA), but rather allosterically enhances the effects of GABA at the receptor level.

For the purpose of this invention, the term "benzodiazepine" (BZ) refers to the benzodiazepine class of drugs that possess sedative, tranquilizing and muscle relaxing properties. These agents are frequently classified as anxiolytic, anticonvulsives, sedatives, and skeletal muscle relaxants. BZs act by binding to the $GABA_A$ receptor of a neuron, possibly causing the receptor to change shape and making it more accessible to GABA. While BZ class of drugs, particularly those that act as full agonists or partial agonists at the $GABA_A$ receptor, are contemplated to be used for the purpose of this invention described herein, BZs that act as antagonists or inverse agonists are not.

For the purpose of this invention, the term "efficacy at the $\alpha_x$ subunit of the $GABA_A$ receptor" or, "efficacy at the $\alpha_y$ and/or $\alpha_z$ subunits of the $GABA_A$ receptor" refers to the effect of a positive allosteric modulator of $GABA_A$ receptor activity, wherein the agent binds to a site independent of the GABA site on a $GABA_A$ receptor comprising $\alpha_x$ subunit, or comprising $\alpha_y$ and/or $\alpha_z$ subunits, and allosterically enhances the effects of GABA at the receptor. By way of example known in the art, BZs do not substitute for GABA to directly activate $GABA_A$ receptors nor do they facilitate opening of the corresponding chloride channel in the absence of GABA. Rather, they act at the BZ site to enhance the action of GABA, particularly through increasing the frequency of the opening of the chloride channel. On the contrary, antagonists or inverse agonists at the BZ site do not have efficacy as a positive allosteric modulator of $GABA_A$ receptors.

For the purpose of this invention, the term "selective for the $\alpha_x$ subunit of the $GABA_A$ receptor" or, "selective for the $\alpha_y$ and/or $\alpha_z$ subunits of the $GABA_A$ receptor" refers to an agent that has efficacy as a positive allosteric modulator at the $\alpha_x$ subunit of the $GABA_A$ receptor or the $\alpha_y$ and/or $\alpha_z$ subunits of the $GABA_A$ receptor at a dose lower than the dose in which the agent has efficacy for GABA receptors comprising other subunits but not the specific aforementioned (i.e., $\alpha_x$ or $\alpha_y$ and/or $\alpha_z$) subunits. For example, a positive allosteric modulator of the $GABA_A$ receptor is "selective" for α1 subunit if the dose required to act as a positive allosteric modulator at one or more, α2, α3 α4, α5, or α6 subunits is at least 50% higher, . . . at least 1-fold higher, at least 2-fold higher, . . . at least 10-fold higher, . . . at least 100-fold higher, . . . at least 1000-fold higher or more than the dose required to act as a positive allosteric modulator at the α1 subunit. The selectivity here refers primarily to functional selectivity of the agent, which may or may not have the corresponding affinity selectivity. It is also specifically contemplated herein that a positive allosteric modulator at the α1 subunit, by itself, can also act as an agonist, an antagonist or inverse agonist at one or more, α2, α3, α4, α5, or α6 subunits. In other embodiments, the agent "selective for $GABA_A$ receptors having α1 subunit" does not act as a selective positive allosteric modulator of $GABA_A$ receptors having other subunits, but not α1 subunit. In that case, the agent may act as an antagonist or inverse agonist on such $GABA_A$ receptors having non-α1 subunits.

For the purpose of this invention, a "short acting" medication, such as a "short acting benzodiazepine", typically has a plasma half-life of approximately 1-12 hours; a "intermediate-acting" medication typically has a plasma half-life of 12-40 hours, while a "long-acting" medication typically has a half-life of 40-250 hours. Here, there may or may not be active metabolites upon metabolism of the parent drug. Often the intermediate- or long-acting BZs are metabolized to active metabolites with long plasma half-lives that exhibit efficacy at the BZ site.

For the purpose of this invention, the concepts of "functional selectivity" and "affinity selectivity" refer to those concepts having been thoroughly reviewed by Atack, J R. (2003), wherein it is stated: "The molecular mechanisms of BZs are now well defined in that they enhance the actions of the inhibitory neurotransmitter GABA by binding to a specific recognition site on $GABA_A$ receptors containing α1, α2, α3 and α5 subunits. Compounds that bind at this modulatory site and enhance the inhibitory actions of GABA are classified as agonists, those that decrease the actions of GABA are termed inverse agonists whereas compounds which bind but have no effect on GABA inhibition are termed antagonists. The clinically used BZs are full agonists and between the opposite ends of the spectrum, i.e., full agonist and full inverse agonist, are a range of compounds with differing degrees of efficacy, such as partial agonists and partial inverse agonists. Attempts have been made to develop compounds which are anxioselective in that they retain the anxiolytic properties of the full agonist BZs but have reduced sedation and dependence (withdrawal) liabilities. Such compounds may interact with all four (i.e., α1, α2, α3 and α5-containing) $GABA_A$ receptor subtypes and have partial rather than full agonist efficacies. Examples of non-selective partial agonists include bretazenil, imidazenil, FG 8205, abecarnil, NS 2710, pagoclone, RWJ-51204 and (S)-desmethylzopiclone. Alternatively, a compound might have comparable binding affinity but different efficacies at the various subtypes, thereby preferentially exerting its effects at subtypes thought to be associated with anxiety (α2- and/or α3-containing receptors) rather than the subtype associated with sedation (α1-containing receptors) . . . . [Development of such] efficacy selective compounds represent a novel approach to targeting specific subtypes of the $GABA_A$ receptor." These are further exemplified by α1-selective agonist displaying sedative and anxiolytic-like properties (Selleri S (2005)), and BZs having sedative but not anxiolytic properties that are mediated by the $GABA_A$ receptor α1-subtype (McKernan, R M et al. (2000)).

The following is a more detailed review of the GABA receptors, and in particular, the GABA α1 receptor, with respect to the autism spectrum disorder (ASD), which can lead to the rationale for the present invention:

A study published by Chen et al. (2014) showed a significant reduction in GABA α1 receptor in post-mortem brain tissue of subjects with autism spectrum disorder (ASD). Another study by Oblak et al. (2011) presented multiple lines of evidence suggesting that GABA system (neurotransmitter GABA and GABA receptor) is disrupted in the brains of individuals with autism, and that altered inhibition within the network influences the ability to perceive emotional expressions. Findings showed a significant reduction in the number of GABA receptors in the cortex of autistic brains, thus likely contributing to the core disturbances of socio-emotional behaviors in autism.

Most recently and perhaps the most significantly, researchers in Harvard and MIT (Robertson et al., 2016) showed that disruption in neurotransmitter GABA signaling in the human autistic brain, thus forging a preliminary path between animal and human GABAergic system models of autism.

Previously, Bauman and Kemper (1994, 2005) found that neuroanatomical studies have revealed structural abnormalities throughout the brains of subjects with autism including frontal (BA9) and parietal (BA40) cortices and cerebellum. The information from various peer-reviewed articles have also identified autistic traits associated with each of these three brain regions. Specifically, Nayate et al. (2005) found that cerebellar abnormalities may be responsible for the dysfunctions within the motor system associated with autism. Abnormalities of the parietal cortex in autism may be associated with visuo-spatial-integration, impaired language, and slowed attention shift between and within modalities (Townsend et al. 1996, Davidovitch et al. 1996). Abnormalities of the frontal cortex are likely to contribute to serious deficiencies in cognition, language, and emotional functions associated with autism (Courchesne et al. 2005).

Fatemi, et al. (2009) demonstrated altered expression in the receptor subunit that my research is focusing on (GABA α1 receptor) as well as in a different subunit of this same receptor (GABA α2 receptor) in the brains of subjects with autism, suggesting dysregulation of the entire system. However while significant reductions in GABA α2 receptor were observed in the parietal cortex (BA40) and the cerebellum, significant reductions in GABA α1 receptor were not only observed in the parietal cortex (BA40) and the cerebellum but in the superior frontal cortex as well. And, as stated above, abnormalities in the frontal cortex are associated with deficiencies in cognition, language, and emotional functions.

DeLorey et al. (2008) evaluated GABA α2 receptor to determine its relation to autistic symptoms. Results showed GABA α2 receptor deficient mice exhibited significant deficits relative to controls in activities related to social behavior including sociability, social novelty, and nesting leading to their conclusion that these behavioral deficits strengthen the face validity of GABA α2 receptor gene deficient mice as being a model of autism spectrum disorder.

In addition to this, many other studies confirmed the link between GABA α2 receptor and autism, see e.g., Buxbaum et al. (2002), including clinical trials involving children affected with autism.

A 2010 report by Weintraub in the MIT Technology Review entitled "A Drug Shows Promise in Autism" caused much excitement in the online autism community. The drug, Arbaclofen, which targets GABA α2 receptor, is closely related to a currently marketed drug, Baclofen, which is a commonly used muscle relaxer and antispastic agent. From an eight week clinical trial of 25 autistic children, unpublished data reported significant improvements in measures of irritability and communications. Overall, the subjects seemed to make eye contact more easily and were less agitated and anxious. Some were able to interact with peers more readily and were less likely to engage in 'stimming'. These findings, however, are preliminary since the study was not placebo-controlled.

In summary, while α2 GABA receptor has been found to be deficient in the cerebellum and parietal cortex of autistic brains, α1 GABA receptor has been found to be deficient in these two regions as well as in the frontal cortex. All three of these regions have been implicated in the pathogenesis of autism. The frontal cortex, specifically, is associated with deficiencies in cognition, language, and emotional functions. In clinical trials, α2 GABA receptor deficient mice exhibited increased autistic symptoms compared to controls. In preliminary trials, certain autistic symptoms of children with autism improved after being administered a drug that targets α2 GABA receptor, which has been found to be deficient in the cerebellum and parietal cortex of the autistic brain.

It was discovered by the present inventor that effective amounts of the drug zolpidem, in a particular oral dosing regimen, can achieve almost complete attenuation of at least one indicium of an ASD, which is, in particular, that of so-called "psychic pain" or "phantom pain." Zolpidem (originally marketed as Ambien® and presently available worldwide under many brand names, as a sedative primarily used for the treatment of insomnia) is a subunit-selective, short-acting non-BZ α1 GABA agonist of the imidazopyridine class. While it similarly binds at the extracellular N-terminal ⟨/© subunit interface of the $GABA_A$ receptors as do BZs, zolpidem differs significantly from classic BZs in chemical structure and neuropharmacological properties. Thus, classic BZs and zolpidem are likely to have different requirements for high-affinity binding to $GABA_A$ receptors (Sancar et al. 2007). On recombinant receptors, zolpidem displays a high affinity to α1-$GABA_A$ receptors, an intermediate affinity to α2- and α3-$GABA_A$ receptors and fails to bind to α5-$GABA_A$ receptors. Studies have shown that the sedative-hypnotic and anticonvulsant activities of zolpidem are due to its action on α1-$GABA_A$ receptors and not on α2- or α3-$GABA_A$ receptors (Crestani F et al., 2000). A recent study showed that Zolpidem is a potent stoichiometry-selective modulator of α1β3 $GABA_A$ receptors and it binds to a novel BZ site in the α1-α1 interface of the $GABA_A$ receptors, a site mimicking the classical α1-γ2 benzodiazepine site (Che Has, A T et al., 2016).

In a more preferred embodiment, the present invention provides that zolpidem with an oral dosing regimen of at least 30 mg every 3.5 hours (around the clock) has been found to be therapeutically effective in almost completely attenuating at least one indicium of an ASD. In at least one subject, the attenuation achieved was found to be immediate and almost complete after the first dose of zolpidem. Especially, the relief of the so-called "psychic pain" or "phantom pain" which was by far the most debilitating symptom of ASD with respect to the subject, was profound after the first dose. The subject has been symptom-free and leading a normal life for at least five years, while on zolpidem with the aforementioned oral dosing regimen.

While not wishing to be bound by theory, it is believed that as provided by the present invention, the medication (zolpidem) profoundly attenuates ASD symptoms by preferentially acting the GABA α1 receptor, which has been shown to have reduced binding sites in the cerebellum, parietal cortex, and the frontal cortex of ASD patients. Further lending support to this belief is the fact that based on the above literature review, a reduced expression of the GABA α1 receptors has been correlated with seizures, which are common among individuals with autism/ASD. However, because the pharmacological profile of zolpidem, as discussed above, also includes an intermediate affinity to α2- and α3-$GABA_A$ receptors, it is further believed that also as provided by the present invention, the medication (zolpidem) profoundly attenuates ASD symptoms by preferentially acting the GABA α1 receptor, while also on other subunits, such as α2- and α3-subunits of the $GABA_A$ receptors, either individually, or in concert. In fact, such potential actions in concert may be important for the relief of multiple ASD symptoms.

Based on the above, the present invention, in one of the embodiments, provides a method of treating an Autism Spectrum Disorder or an indicium thereof, in a subject in need thereof, which method comprises administering to said subject a therapeutically effective amount of a composition comprising a compound and a pharmaceutically acceptable carrier, wherein said compound is a positive allosteric modulator of the $GABA_A$ receptor, or a pharmaceutically acceptable salt thereof, that is receptor subunit-selective. The selectivity can be function, or affinity-based, or both; and can be towards, primarily, an α1 subunit and an α2, α3 or α3 subunit or a combination thereof.

Based upon the aforementioned difference in structures, while similarity in binding sites between zolpidem and the BZs, it is also contemplated in other embodiments of the present invention that other compounds having their mechanisms of actions similar to zolpidem, particularly those that are full agonists or partial agonists at the $GABA_A$ receptors, can also be used with the methods described in the present application. These compounds can be of the BZ family. In some embodiments, the BZ drug is a short-acting BZ class compound. In other embodiments, the BZ drug is a long-acting BZ class compound. In some embodiments, the BZ drug is a typical BZ class compound. In other embodiments, the BZ drug can be an atypical BZ class compound. In some embodiments, the BZ drug acts on the α1-subtype of the $GABA_A$ receptor (e.g., has a functional selectivity at the α1 subunit). In another embodiment, the BZ drug is selective for the α1 subunit, as well as other subunits, such as the α2 and/or α3 subunits, etc., of the $GABA_A$ receptor.

Alternatively, it is further contemplated in still other embodiments of the present invention that other compounds having their mechanisms of actions similar to zolpidem, and thus, also capable of being used with the methods described in the present application, can be of the non-BZ family. In some embodiments, the non-BZ drug is a short-acting non-BZ compound. In other embodiments, the non-BZ drug is a long-acting non-BZ compound. In some embodiments, the non-BZ drug acts on the α1-subtype of the $GABA_A$ receptor (e.g., has a functional selectivity at the α1 subunit). In another embodiment, the non-BZ drug is selective for the α1 subunit, as well as other subunits, such as the α2 and/or α3 subunits, etc., of the $GABA_A$ receptor.

For clinical use, zolpidem, or an alternative compound, as aforementioned, and optionally in combination with another subunit-selective $GABA_A$ receptor agonist, is suitably formulated into pharmaceutical formulations for oral administration in accordance with embodiments of the present invention. Thus, zolpidem, or an alternative compound, as aforementioned, and optionally in combination with another subunit-selective $GABA_A$ receptor agonist, is formulated with a pharmaceutically and pharmacologically acceptable carrier or adjuvant. The carrier may be in the form of a solid, semi-solid or liquid diluent.

A further aspect of the invention is the use of zolpidem, or an alternative compound, as aforementioned, and optionally in combination with another subunit-selective $GABA_A$ receptor agonist, for the manufacture of a medicament for the treatment of ASD.

A further aspect of the invention is a method for the treatment or prevention of ASD, whereby a pharmaceutically and pharmacologically effective amount of zolpidem, or an alternative compound, as aforementioned, and optionally in combination with another subunit-selective $GABA_A$ receptor agonist, is administered to a subject in need of such treatment.

In the preparation of oral pharmaceutical formulations in accordance with the present invention, zolpidem, or an alternative compound, as aforementioned, and optionally in combination with another subunit-selective $GABA_A$ receptor agonist, to be formulated is mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or compressed into tablets.

Soft gelatin capsules may be prepared with capsules containing a mixture of zolpidem, or an alternative compound, as aforementioned, and optionally in combination with another subunit-selective $GABA_A$ receptor agonist, with vegetable oil, fat, or other suitable vehicle for soft gelatin capsules. Hard gelatin capsules may contain zolpidem, or an alternative compound, as aforementioned, and optionally in combination with another subunit-selective $GABA_A$ receptor agonist, in combination with solid powdered ingredients such as lactose, saccharose, sorbitol, mannitol, potato starch, corn starch, amylopectin, cellulose derivatives or gelatin.

Liquid preparations for oral administration may be prepared in the form of syrups or suspensions, e.g. solutions or suspensions, containing zolpidem, or an alternative compound, as aforementioned, and optionally in combination with another subunit-selective $GABA_A$ receptor agonist, and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agents. Liquid preparations for oral administration may also be prepared in the form of a dry powder to be reconstituted with a suitable solvent prior to use.

In one aspect of the present invention, zolpidem, or an alternative compound, as aforementioned, and optionally in combination with another subunit-selective $GABA_A$ receptor agonist, may be administered multiple times daily, depending on the severity of the patient's condition. A preferred daily dose of zolpidem is within the range of 0.01 mg to 120 mg, but this will depend on various factors such as the route of administration, the age and weight of the patient as well as of the severity of the patient's condition. A more preferred dose regimen for zolpidem is at least 30 mg every 3.5 hours around the clock for an adult of about 50-70 Kg.

The many elements of the present invention make it unique in the field. The novelty is illustrated by the various options for nearly every aspect of the invention that allow it to be used in the proper exercise form by a variety of users, both in terms of body size and fitness level. Additionally, there is a wide range of exercises available to any user of the present invention, and users can perform exercises that use the upper and lower extremity muscle groups simultaneously.

Although this invention has been described with a certain degree of particularity, it is to be understood that the present disclosure has been made only by way of illustration and that numerous changes in the details of construction and arrangement of parts may be resorted to without departing from the spirit and the scope of the invention.

REFERENCES

Baron-Cohen, S., Scott, F. J., Allison, C., Williams, J., Bolton, P., Matthews, F. E., Brayne, C., Prevalence of autism-spectrum conditions: UK school-based population study. *Br. J. Psychiatry* 194 (2009) 500-9.

Schechter, R., Grether, J. K., Continuing increases in autism reported to California's developmental services system: mercury in retrograde. *Arch. Gen. Psychiatry.* 65 (2008) 19-24.

Thomas, P., Zahorodny, W., Peng, B., Kim, S., Jani, N., Halperin, W., Brimacombe, M., The association of autism diagnosis with socioeconomic status. Autism, (2011) 218-228.

Zaroff, C. M., Uhm, S. Y., Prevalence of autism spectrum disorders and influence of country of measurement and ethnicity. *Soc. Psychiatry. Psychiatr. Epidemiol.* 47 (2011) 395-398.

Allely, C. S., Pain sensitivity and observer perception of pain in individuals with autistic spectrum disorder. *Sci World J* 2013 (2013) 916178.

Moore D. J., Acute pain experience in individuals with autism spectrum disorders: a review, *Autism.* 19(4) (2015) 387-99.

Clarke, C., Autism Spectrum Disorder and Amplified Pain, *Case Rep Psychiatry* 2015 (2015) 930874.

Craig, M. C., Zaman, S. H., Daly, E. M., Cutter, W. J., Robertson, D. M., Hallahan, B., Toal, F., Reed, S., Ambikapathy, A., Brammer, M., Murphy, C. M., Murphy, D. G., Women with autistic-spectrum disorder: magnetic resonance imaging study of brain anatomy. *Br. J. Psychiatry.* 191 (2007) 224-8.

Ecker, C., Marquand, A., Mourao-Miranda, J., Johnston, P., Daly, E. M., Brammer, M. J., Maltezos, S., Murphy, C. M., Robertson, D., Williams, S. C., Murphy, D. G., Describing the brain in autism in five dimensionsemagnetic resonance imaging-assisted diagnosis of autism spectrum disorder using a multiparameter classification approach. *J. Neurosci.* 30 (2010) 10612-10623.

Hallahan, B., Daly, E. M., McAlonan, G., Loth, E., Toal, F., O'Brien, F., Robertson, D., Hales, S., Murphy, C., Murphy, K. C., Murphy, D. G., Brain morphometry volume in autistic spectrum disorder: a magnetic resonance imaging study of adults. *Psychol. Med.* 39 (2009) 337-346.

Pizzarelli, R., Cherubini, E., Alterations of GABAergic signaling in autism spectrum disorders. *Neural. Plast.* (2011) 297153.

Rubenstein, J. L., Merzenich, M. M., Model of autism: increased ratio of excitation/inhibition in key neural systems. *Genes. Brain. Behav.* 2 (2003) 255-267.

Yizhar, O., Fenno, L. E., Prigge, M., Schneider, F., Davidson, T. J., O'Shea, D. J., Sohal, V. S., Goshen, I., Finkelstein, J., Paz, J. T., Stehfest, K., Fudim, R., Ramakrishnan, C., Huguenard, J. R., Hegemann, P., Deisseroth, K., Neocortical excitation/inhibition balance in information processing and social dysfunction. Nature 477 (2011) 171-178.

Atack, J R., Anxioselective compounds acting at the GABA (A) receptor benzodiazepine binding site, *Curr Drug Targets CNS Neurol Disord.* 2(4) (2003) 213-32

Selleri S, Bruni F, Costagli C, Costanzo A, Guerrini G, Ciciani G, Gratteri P, Besnard F, Costa B, Montali M, Martini C, Fohlin J, De Siena G, Aiello P M., A novel selective GABA(A) alpha1 receptor agonist displaying sedative and anxiolytic-like properties in rodents, *J Med Chem.* 48(21): (2005) 6756-60

McKernan, R M., Rosahl T W, Reynolds D S, Sur C, Wafford K A, Atack J R, Farrar S, Myers J, Cook G, Ferris P, Garrett L, Bristow L, Marshall G, Macaulay A, Brown N, Howell O, Moore K W, Carling R W, Street L J, Castro J L, Ragan C I, Dawson G R, Whiting P J., Sedative but not anxiolytic properties of benzodiazepines are mediated by the GABA(A) receptor alpha1 subtype. *Nat Neurosci.* 3(6) (2000) 587-92.

Chen C H, Huang C C, Cheng M C, Chiu Y N, Tsai W C, Wu Y Y, Liu S K, Gau S S., Genetic analysis of GABRB3 as a candidate gene of autism spectrum disorders *Mol Autism.* 5 (2014) 36.

Oblak A L, Gibbs T T, Blatt G J., Reduced GABAA receptors and benzodiazepine binding sites in the posterior cingulate cortex and fusiform gyrus in autism, *Brain Res.* 1380 (2011) 218-28.

Robertson, Caroline et al., Reduced GABAergic Action in the Autistic Brain, *Cur. Biol.* 26(1) (2016) 80-85.

Bauman, Margaret L., and Thomas L. Kemper. "Neuroanatomic observations of the brain in autism." *The neurobiology of autism* 612 (1994) 119-145.

Bauman, Margaret L., and Thomas L. Kemper. *The neurobiology of autism.* JHU Press, 2005.

Nayate, Ashwini, John Bradshaw and Nicole Rinehart. Autism and Asperger's disorder: are they movement disorders involving the cerebellum and/or basal ganglia? *Brain Res Bull.* 67(4) (2005) 327-334.

Townsend, Jeanne, Naomi Singer Harris, and Eric Courchesne. "Visual attention abnormalities in autism: Delayed orienting to location." *J. Int. Neuropsychological Soc.* 2(6) (1996): 541-550.

Davidovitch, M., Patterson, B., Gartside, P. Head circumference measurements in children with autism. *J. Child Neurology,* 11 (1996) 389-393.

Courchesne, Eric, and Karen Pierce. "Why the frontal cortex in autism might be talking only to itself: local over-connectivity but long-distance disconnection." *Current opinion in neurobiology* 15(2) (2005) 225-230.

Fatemi, S. Hossein, et al. "GABAA receptor downregulation in brains of subjects with autism." *J. autism developmental disorders* 39(2) (2009) 223-230.

DeLorey, Timothy M., et al. "Gabrb3 gene deficient mice exhibit impaired social and exploratory behaviors, deficits in non-selective attention and hypoplasia of cerebellar vermal lobules: a potential model of autism spectrum disorder." Behavioural brain research 187(2) (2008) 207-220.

Buxbaum, J. D., et al. "Association between a GABRB3 polymorphism and autism." Mol. Psychiatry, 7(3) (2002) 311-6.

Weintraub Karen "A Drug Shows Promise in Autism—A chemical that alters chemical signaling seems to ease anxiety and other symptoms" (2010) retrievable at MIT Technology Review: www.technologyreview.com.

Sancar F, Ericksen S S, Kucken A M, Teissére J A, Czajkowski C., Structural determinants for high-affinity zolpidem binding to GABA-A receptors, *Mol Pharmacol.* 71(1) (2007) 38-46. Epub 2006 Sep. 29.

Florence Crestani, James R Martin, Hanns Möhler, and Uwe Rudolph, Mechanism of action of the hypnotic zolpidem in vivo, *Br J Pharmacol.* 131(7) (2000) 1251-1254.

Che Has A T, Absalom N, van Nieuwenhuijzen P S, Clarkson A N, Ahring PK1, Chebib M, Zolpidem is a potent stoichiometry-selective modulator of α1β3 GABAA receptors: evidence of a novel benzodiazepine site in the α1-α1 interface, *Sci Rep.,* 27; 6 (2016): 28674.

What is claimed is:

1. A method of treating an Autism Spectrum Disorder (ASD) or an indicium thereof, in a subject in need thereof, which method comprises administering to said subject a therapeutically effective amount of zolpidem,
    wherein said therapeutically effective amount of zolpidem comprises a daily dose of zolpidem within the range of 0.01 mg to 120 mg, and
    wherein said therapeutically effective amount of zolpidem comprises a daily dose of zolpidem of at least 30 mg every 240 minutes.

2. A method for reducing or ameliorating at least one indicium of an Autism Spectrum Disorder (ASD), the method comprising: administering an effective amount of zolpidem that increases the response of the GABAA receptor to endogenous GABAergic transmission, whereby at least one indicium is reduced or ameliorated,
    wherein said therapeutically effective amount of zolpidem comprises a daily dose of zolpidem within the range of 0.01 mg to 120 mg, and
    wherein said therapeutically effective amount of zolpidem comprises a daily dose of zolpidem of at least 30 mg every 240 minutes.

* * * * *